(12) United States Patent
Tokunaga et al.

(10) Patent No.: US 6,222,074 B1
(45) Date of Patent: Apr. 24, 2001

(54) PROCESS FOR PREPARATION OF 4,6-DIAMINORESORCINOL OR SALTS THEREOF

(75) Inventors: Kenichi Tokunaga; Motohito Shiratori, both of Funabashi; Kazuhiko Akimoto, Nei-gun; Hideo Suzuki; Isao Hashiba, both of Funabashi, all of (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 09/600,551

(22) PCT Filed: Jan. 25, 1999

(86) PCT No.: PCT/JP99/00268

§ 371 Date: Jul. 25, 2000

§ 102(e) Date: Jul. 25, 2000

(87) PCT Pub. No.: WO99/37601

PCT Pub. Date: Jul. 29, 1999

(30) Foreign Application Priority Data

Jan. 27, 1998 (JP) .................................................. 10-013684

(51) Int. Cl.⁷ .................................................. C07C 213/02
(52) U.S. Cl. .......................... 564/415; 564/442; 564/443
(58) Field of Search .................................... 564/415, 442, 564/443

(56) References Cited

U.S. PATENT DOCUMENTS 5,453,542 * 9/1995 Morgan et al. .

FOREIGN PATENT DOCUMENTS

| 61-501452 | * | 7/1986 | (JP) . |
| 2-229143 | | 9/1990 | (JP) . |
| 9-19443 | * | 9/1995 | (JP) . |
| 7-242604 | | 9/1995 | (JP) . |
| 9-124575 | | 5/1997 | (JP) . |
| 9-157239 | | 6/1997 | (JP) . |
| 10-168040 | * | 6/1998 | (JP) . |

* cited by examiner

Primary Examiner—Samuel Barts
(74) Attorney, Agent, or Firm—Oliff & Berridge, PLC

(57) ABSTRACT

The invention relates to a process for preparation of 4,6-diaminoresorcinol or salts thereof by reducing 4,6-bis(substituted)phenylazoresorcinol expressed by the formula [1]

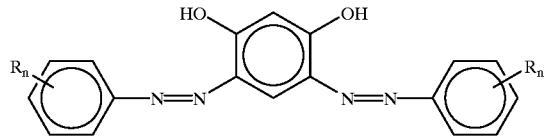

[1]

wherein, R denotes a halogen atom, an alkyl group having 1–5 carbon atoms, a hydroxycarbonyl group or an alkoxy group having 1–5 carbon atoms, n denotes 0 or any integer of 1–5, and two or more groups R may be same or different each other, for example, 4,6-bisphenylazoresorcinol, with hydrogen in the presence of a metal catalyst to obtain 4,6-diaminoresorcinol or salts thereof, characterized in that an aliphatic nitrile compound (for example, acetonitrile) is used as a solvent, or characterized in that the reduction is carried out by using at least one organic solvent selected from aliphatic nitrile compounds, aliphatic alcohols having 3–5 carbon atoms, dioxane and ethylene glycol monomethyl ether, etc. as a solvent and furthermore in the presence of a filter aid (for example, active carbon). According to the said preparation process, 4,6-diaminoresorcinol with high purity can be easily obtained from 4,6-bis(substituted) phenylazoresorcinol in a high yield.

17 Claims, No Drawings

PROCESS FOR PREPARATION OF 4,6-DIAMINORESORCINOL OR SALTS THEREOF

This application is a 371 of PCT/JP99/00268 filed Jan. 25, 1999.

FIELD OF THE INVENTION

The present invention relates to a process for preparation of 4,6-diaminoresorcinol or salts thereof. More precisely, the invention relates to a process for preparation of 4,6-diaminoresorcinol or salts thereof by reducing 4,6-bis(substituted)phenylazoresorcinol.

4,6-Diaminoresorcinol is a monomer for polybenzoxazole, and polybenzoxazole is a polymer having high strength and high elastic modulus as well as characteristics superior in thermal resistance and chemical resistance (see the Japanese Translation of PCT International Patent Publication No. Sho 6I-501452 official gazette and the Japanese Patent Open-laid Publication No. Hei 2-229143 official gazette).

BACKGROUND ART

Reduction of 4,6-bisphenylazoresorcinol is generally carried out with hydrogen by using a noble metal catalyst (the Japanese Patent Open-laid Publication No. Hei 7-242604 official gazette). According to the Japanese Patent Open-laid Publication No. Hei 7-242604 official gazette, the reduction is carried out under a neutral condition in a solvent. As to the solvent, there is described that water, lower alcohols, aromatic hydrocarbons, halogen-substituted benzenes, halogenated aliphatic hydrocarbons, ethers, lower ketones are used alone or in combination. Furthermore, as the post-treatment after the end of the reduction reaction, two methods are described. In a first method, an acid is added and an acid salt is formed after filtration through Celite still under a nitrogen atmosphere to obtain 4,6-diaminoresorcinol, which is filtered off the catalyst and Celite, thereafter purified and isolated. In a second method, an acid is added to the reaction solution to make a salt, which is dissolved, filtered off the catalyst, thereafter purified and isolated.

The former has such effects that recovery of aniline produced in the reaction is easy and that the purification procedure is simple, but filterability is very slow. A yield is low such as 60% due to the loss of 4,6-diaminoresorcinol into the filtrate, thus the method cannot be said as an industrial method.

The latter has high stability in air and good operability since an acid is added to make a salt. Furthermore, filterability is high, which seldom cause any problem. But, it has such a disadvantage that separation and purification of a by-product, aniline, and 4,6-diaminoresorcinol become very complicated due to the presence thereof in an acidic solution.

In the reduction of 4,6-bis(substituted)phenylazoresorcinol, 2 equivalents of an aniline derivative is by-produced in addition to 4,6-diaminoresorcinol. It is the largest problem in the reduction process of 4,6-bis(substituted)phenylazoresorcinol how simply the aniline derivative can be separated with a few loss of an objective 4,6-diaminoresorcinol produced.

DISCLOSURE OF THE INVENTION

We, inventors, have studied eagerly and found an industrial process for operating freely 4,6-diaminoresorcinol to complete the present invention. That is, 4,6-diaminoresorcinol is obtained in a high yield by reducing a 4,6-bisphenylazoresorcinol derivative in a selected solvent in the presence of a noble metal catalyst with hydrogen.

However, filterability is sometimes very slow depending on the kind of the solvent. For these cases, filterability is eminently improved by adding a filter aid such as active carbon into the reaction.

An object of the invention is to provide a process by which 4,6-diaminoresorcinol having high purity can be obtained easily in a high yield from 4,6-bis(substituted)phenylazoresorcinol. Thereby, a recovery rate of the aniline derivative is improved, which is economically advantageous.

The inventors have studied eagerly and thus found a process to solve the above-mentioned subject to complete the present invention. That is, the present invention relates to a process for preparation of 4,6-diaminoresorcinol or salts thereof (herein, salts thereof mean acid salts of 4,6-diaminoresorcinol, which meaning is referred to same in the followings) by reducing 4,6-bis(substituted)phenylazoresorcinol expressed by the formula [1]

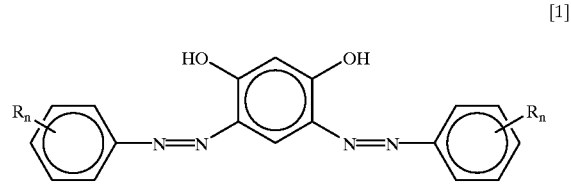

[1]

wherein, R denotes a halogen atom, an alkyl group having 1–5 carbon atoms, a hydroxycarbonyl group or an alkoxy group having 1–5 carbon atoms, n denotes 0 or any integer of 1–5, and two or more groups R may be same or different each other, with hydrogen in the presence of a metal catalyst to obtain 4,6-diaminoresorcinol or salts thereof, characterized in that an aliphatic nitrile compound is used as a solvent.

Furthermore, the invention also relates to a process for preparation of 4,6-diaminoresorcinol or salts thereof by reducing 4,6-bis(substituted)phenylazoresorcinol expressed by the formula [1] above with hydrogen in the presence of a metal catalyst and a solvent to obtain 4,6-diaminoresorcinol or salts thereof, characterized in that at least one organic solvent selected from aliphatic nitrile compounds, aliphatic alcohols having 3–5 carbon atoms, ethylene glycol monomethyl ether, ethylene glycol monoethyl ether, diethylene glycol monoethyl ether and dioxane is used as the solvent and that the reduction is carried out furthermore in the presence of a filter aid.

4,6-Bis(substituted)phenylazoresorcinol which is the starting material in the invention can be obtained by diazotizing a (substituted) aniline expressed by the formula [2]

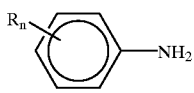

wherein, R and n are defined same as in the formula [1], to obtain a (substituted) benzene diazonium salt and subjecting the diazonium salt to the coupling reaction with resorcinol. Specifically, the (substituted) benzene diazonium salt is obtained by adding dropwise 2.5–4 equivalents, based on aniline, of an inorganic acid into a mixture of substituted aniline and 5–10 times by weight of water with cooling and then adding dropwise 1–1.5 times by mole of sodium nitrite or potassium nitrite dissolved in 2–3 times by weight, based on (substituted) aniline, of water into the mixed solution. As the inorganic acid, at least one inorganic acid selected from hydrochloric acid, hydrobromic acid, sulfuric acid and phosphoric acid is used. Hydrochloric acid is preferable industrially and economically amongst of these inorganic acids.

Specifically, there may be mentioned for example aniline, 2-chloroaniline, 4-chloroaniline, 2,6-dichloroaniline, o-toluidine, m-toluidine, p-toluidine, anthranilic acid, o-anisidine, m-anisidine and p-anisidine, and it is preferable to use any of these anilines. Aniline is the most preferable from the viewpoints of economical efficiency and stability of the compound etc.

As the coupling reaction of a (substituted) benzene diazonium salt with resorcinol, any known methods may be used, but the following methods are preferable; a method to react a (substituted) benzene diazonium salt expressed by the formula [3]

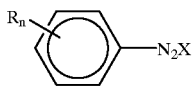

wherein, R and n are defined same as in the formula [1], and X denotes Cl, Br, $OSO_3H$ or $OPO_3H_2$, in a solvent which is made alkaline which is filed as Japanese Patent Laid-open Publication No. Hei 9-124575 by the present applicant, and a method to mix a solution of the (substituted) benzene diazonium salt expressed by the formula [3] with a solution or suspension of an alkali metal or alkali earth metal hydroxide to obtain a mixed solution made alkaline and mix to react the solution with resorcinol and/or its alkali metal salt or alkali earth metal salt which is filed as Japanese Patent Laid-open Publication No. Hei 9-157239.

4,6-bis(substituted)phenylazoresorcinol which is the raw material in the invention is, therefore, one obtained by reacting resorcinol with an alkaline (substituted) benzene diazonium salt to make acidic, thereafter collecting by filtration and washing with water. It may be used as such or may be used after dried. Dried one is preferable from the viewpoint of a yield in the reduction reaction, since contamination from water causes much escape of 4,6-diaminoresorcinol into a filtrate. As the reaction mixture is used without any purification, purity of 4,6-bis(substituted) phenylazoresorcinol is about 80%, and additionally 4-phenylazoresorcinol, 2,4,6-triphenylazoresorcinol and ones of unknown structure may be obtained therein, which is not a big problem. Of course, those in which this mixture is purified by recrystallization with toluene etc. may be used with a good result, but purification of 4,6-bisphenylazoresorcinol is very difficult owing to low solubility thereof.

Next, the reduction process of 4,6-bis(substituted) phenylazoresorcinol with hydrogen in the presence of the metal catalyst and the solvent is described. As the solvent used for the reduction reaction, there may be used at least one organic solvent selected from aliphatic nitrile compounds, aliphatic alcohols having 3–5 carbon atoms, ethylene glycol monomethyl ether, ethylene glycol monoethyl ether, diethylene glycol monoethyl ether and dioxane. Methanol and ethanol have an economical problem since 4,6-diaminoresorcinol is escaped much into the filtrate for those cases. Those other than nitriles have such problems that filterability is quite slow during collection by filtration of produced 4,6-diaminoresorcinol and that the industrial operation has thus a problem. During it, filterability is much improved by adding a filter aid into the reaction.

On the other hand, nitriles are preferable because of good filterability and a small amount of escape into the filtrate. Addition of the filter aid is also effective for improvement in filterability for the cases of nitriles.

As the filter aid, there may be used active carbon, Celite, active clay and cellulose, wherein active carbon is particularly preferable.

An amount of the filter aid is 1–100% by weight relative to 4,6-bis(substituted)phenylazoresorcinol, but it may be higher for the cases of low filterability and may be lower for the cases of good one. Preferably, it is 5–30% by weight. Addition of the filter aid into the reaction system is effective not only for improvement in filterability but also for shortening of the reaction period. It may adsorb impurities in the raw materials to prevent deterioration of the catalyst. Furthermore, occasionally, improvement in filterability can be obtained by addition of the filter aid even after the end of the reaction.

As aliphatic nitrile compounds, monocyano compounds having 2–6 carbon atoms are preferable. Specifically, there may be mentioned acetonitrile, propionitrile, butyronitrile, isobutyronitrile, valeronitrile, isovaleronitrile, trimethylacetonitrile, hexanenitrile and 4-methylvaleronitrile etc. As particularly preferable ones, there may be mentioned fast reacting and economically inexpensive acetonitrile, propionitrile, butyronitrile and isobutyronitrile etc.

More specifically speaking, for the cases that 4,6-bisphenylazoresorcinol is used as the reaction substrate, a reaction yield of 4,6-diaminoresorcinol is 98–99%, a crystalline yield of 4,6-diaminoresorcinol is 93–96%, a yield of aniline in crude crystals of 4,6-diaminoresorcinol is 1–2%, thus 4,6-diaminoresorcinol having high purity can be isolated in a high yield as crystals. On the other hand, an approximately theoretical amount of aniline is contained in the filtrate.

An amount of the solvent to be used is 1–50 times by weight, preferably 2–20 times by weight, based on 4–6bis (substituted)phenylazoresorcinol.

The metal catalyst used in the invention is at least one metal selected from copper and the Group 8 elements in the periodic table. As the Group 8 elements in the periodic table, there may be mentioned platinum, palladium, ruthenium, rhodium, nickel, cobalt and iridium etc. Platinum and palladium are preferable amongst of these metal catalysts, since 4,6-diaminoresorcinol can be obtained in a high yield with them.

As the form of the catalyst, there may be mentioned simple substances such as palladium black and platinum black; alloys such as Raney nickel and cobalt; metal salts such as palladium chloride and palladium acetate; metal oxides such as copper oxide and platinum oxide; metal complex such as acetylacetone copper and acetylacetone palladium; and supported metals on carbon or oxides such as silica, alumina, zirconia, titania and zeolite. Supported metals are particularly preferable amongst of them from the viewpoints of recovery and reuse, wherein palladium-carbon and platinum-carbon are preferable. In particular, platinum-carbon is preferable due to its higher activity than palladium-carbon in spite of a fewer supported amount.

Furthermore, a multi-elemental metallic catalyst in which a second metal is added to a first metal such as platinum, palladium or ruthenium may be used, with the object for improving activity and with the object for suppressing deterioration due to the reaction and the acidic treatment to make reuse possible. It is preferable that one or more of rhenium, iridium, tin, antimony, germanium, indium and rhodium is(are) added as the second metal(s) to the first metal in an amount of 2–50 atomic molar %.

Specifically, there may be mentioned for example 5% Pd/1% Re—C, 5% Pd/2% In—C, 2% Pt/0.5% Re—C, 1% Pt/0.2% Ge—C, etc.

An amount of the catalyst to be used is preferably 0.0005–10% by weight as a metal content relative to 4,6-bis(substituted)phenylazoresorcinol, and in particular the catalyst is used in an amount of 0.001–10% by weight.

The pressure of hydrogen is from the normal pressure to 10000 kPa, preferably from the normal pressure to 1000 kPa. The reaction temperature can be at from –10 to 150° C., preferably it is 0–100° C., more preferably 10–80° C.

In the reaction solution, 4,6-diaminoresorcinol is present as a solid form. The removal method thereof is illustrated as follows. 4,6-Diaminoresorcinol can be obtained together with the catalyst and the filter aid by filtering without contact with air. Aniline is taken into the filtrate, but if filterability is slow, the content of the cake becomes much and removal of aniline becomes insufficient, thus it is washed with a small amount of the reaction solvent, lower alcohol or water.

Since 4,6-diaminoresorcinol is unstable to oxidation in its free form at the normal temperature, it is necessary to add an acid to make a salt thereof. As the acid, there may used hydrochloric acid, hydrobromic acid, sulfuric acid and phosphoric acid, wherein hydrochloric acid is most preferable industrially. It may be added to 2 or more times by mole of an aqueous hydrochloric acid solution to dissolve with heating, or 2 or more times by mole of an aqueous hydrochloric acid solution may be added on a funnel to dissolve or suspend, removed, and dissolved with heating. The insoluble substances are filtered off, and, if necessary, an active carbon treatment is carried out. Active carbon is filtered off, hydrochloric acid is added, and then 4,6-diaminoresorcinol hydrochloride deposited by cooling is collected by filtration. Active carbon has an eminent effect for decoloring.

When 4,6-diaminoresorcinol is dissolved by using an aqueous hydrochloric acid solution, hydrochloric acid is used in an amount of 2–10 times by mole, wherein 2–3 times by mole relative to 4,6-diaminoresorcinol is preferable, since solubility is lowered with much hydrochloric acid. Water is used in an amount of 1–20 times by part relative to 4,6-diaminoresorcinol, wherein 3–10 times by part are preferable from the viewpoint of relationships with solubility and crystallization. A necessary amount of active carbon is varied according to the coloration degree and the object, but it is 0–100% by weight, preferably 5–30% by weight.

After the active carbon treatment, solids are deposited by salting out with addition of concentrated hydrochloric acid, and an amount of added hydrochloric acid may be 4–20 times by mole of 4,6-diaminoresorcinol. It is influenced by the amount of water from the economical viewpoint, but 4–8 times by mole are preferable. 4,6-Diaminoresorcinol dihydrochloride is obtained by drying after filtration.

Although 4,6-diaminoresorcinol dihydrochloride is also susceptible to oxidation, addition of stannous chloride has a resistant effect on oxidation.

BEST MODE FOR CARRYING OUT THE INVENTION

The above-mentioned reduction reaction may be carried out continuously.

The invention of the present application is illustrated by Examples as follows, but the invention is not limited thereto.

REFERENCE EXAMPLE 1

A solution of 30 g of sodium nitrite dissolved in 55 g of water was added dropwise into a mixed solution of 41 g of aniline, 98 g of 35% hydrochloric acid and 100 g of water at 0–5° C., to synthesize an aqueous solution of benzenediazonium chloride. The aqueous solution of benzenediazonium chloride was added dropwise into a mixed solution comprising 55 g of sodium hydroxide and 110 g of water at below 10° C.

The mixed solution was added dropwise into a mixed solution comprising 22 g of resorcinol, 24 g of sodium hydroxide and 22 g of water at 10° C. for 40 minutes. After the end of the dropwise addition, it was stirred at 10° C. for 3 hours. After the end of the reaction, hydrochloric acid was added to the reaction mixture to make it acidic, and deposited solids were collected by filtration, washed with water and dried, to obtain 62 g of dark red solids. Purity of 4,6-bisphenylazoresorcinol was 79.5%, and about 5% of 2,4,6-triphenylazoresorcinol was contained therein.

EXAMPLE 1

10.0 g (0.025 mol) of 4,6-bisphenylazoresorcinol (purity; 79.5%), 50 g of acetonitrile and 2.0 g of 5% Pd—C were introduced in a 100 ml autoclave made by Hastelloy, to react them at a stirring rate of 600 rpm and at 30° C. with supplying hydrogen under a constant pressure of 300 kPa from a hydrogen pressurized vessel. A pressure decrease in the hydrogen pressurized vessel was stopped after the reaction period of 2.5 hours. After the stirring was stopped, the temperature of the autoclave was returned to the room temperature and the reactant was removed after nitrogen substitution. The slurry reactant was separated into a cake and a filtrate by filtration under a nitrogen atmosphere. The filtration period was 20 minutes. The cake was washed with acetonitrile to obtain a wetted product. The wetted product and the filtration wash liquid were subjected to the following analysis as their hydrochlorides.

That is, yields of 4,6-diaminoresorcinol (DAR) and aniline produced in the wetted product and the filtration wash liquid were analyzed by liquid chromatography. Results are shown in Table 1. A yield of DAR in the wetted product was 92.5% and a yield in the filtration wash liquid was 4.5%, so that a total yield was 97%. A yield of aniline in the wetted product was 1.5% and a yield in the filtration wash liquid was 222.0%, so that a total yield was 223.5%.

The reason why the aniline yield being above 200% was liberation of aniline caused by hydrogenolysis of 4-azoresorcinol and 2,4,6-triazoresorcinol contained as impurities in the raw material.

COMPARATIVE EXAMPLE 1

The reduction reaction was carried out similar to Example 1 except that the solvent in Example 1 was replaced by isopropanol. As the filtration period was not finished after about 1 hour, the following treatments were discontinued.

returned to the room temperature and the reactant was removed after nitrogen substitution. The slurry reactant was separated into a cake and a filtrate by filtration under a nitrogen atmosphere. The filtration period was 10 minutes. The cake was washed with acetonitrile to obtain a wetted product. They were analyzed similar to Example 1. A yield of DAR in the wetted product was 93.1% and a yield in the filtration wash liquid was 4.9%, so that a total yield was 98.0%. A yield of aniline in crystals was 1.5% and a yield in the filtration wash liquid was 222.0%, so that a total yield was 223.5%.

EXAMPLES 3–11 AND COMPARATIVE EXAMPLES 2–6

The reaction was carried out similar to Example 2 except that acetontrile in Example 2 was replaced by other solvents. Results are shown in Table 1. Herein, the filtration periods were all within 30 minutes.

TABLE 1

| | Solvent | Reaction period (hr) | DAR yield % | | | Aniline yield % | | |
|---|---|---|---|---|---|---|---|---|
| | | | Crystal | Filtration wash liquid | Total | Crystal | Filtration wash liquid | Total |
| Example | | | | | | | | |
| 2 | $CH_3CN$ | 2.5 | 93.1 | 4.9 | 98.0 | 1.5 | 222.0 | 223.5 |
| 3 | $CH_3CH_2CN$ | 4 | 95.3 | 3.1 | 98.4 | 1.2 | 222.8 | 224.0 |
| 4 | $(CH_3)_3CCN$ | 6 | 96.6 | 2.2 | 98.8 | 1.1 | 223.1 | 224.2 |
| 5 | n-PrOH | 3.5 | 84.5 | 10.8 | 94.8 | 2.4 | 224.4 | 226.8 |
| 6 | i-PrOH | 4 | 87.0 | 7.4 | 94.4 | 18.5 | 205.3 | 223.8 |
| 7 | n-BuOH | 3 | 86.9 | 7.9 | 94.8 | 3.1 | 221.8 | 224.5 |
| 8 | sec-BuOH | 6 | 84.9 | 8.0 | 92.9 | 5.6 | 213.1 | 218.7 |
| 9 | n-PeOH | 6 | 87.6 | 4.8 | 92.4 | 4.4 | 217.4 | 221.8 |
| 10 | $CH_3OC_2H_4OH$ | 6 | 87.6 | 4.8 | 92.4 | 4.4 | 217.4 | 221.8 |
| 11 | 1,4-Dioxane | 14 | 85.1 | 5.9 | 91.0 | 5.2 | 220.2 | 225.4 |
| Comparative Example | | | | | | | | |
| 2 | MeOH | 2 | 58.1 | 34.2 | 92.3 | 2.7 | 225.4 | 228.1 |
| 3 | EtOH | 2 | 75.4 | 18.9 | 94.3 | 2.6 | 222.8 | 225.4 |
| 4 | Toluene | 17 | Conversion rate 15% | | | | | |
| 5 | o-Dichlorobenzene | 21 | Conversion rate 70% | | | | | |
| 6 | Ethyl acetate | 20 | Conversion rate 15% | | | | | |

EXAMPLE 2

10.0 g (0.025 mol) of 4,6-bisphenylazoresorcinol (purity; 79.5%), 50 g of acetonitrile and 2.0 g of 5% Pd—C and 1.0 g of active carbon were introduced in a 100 ml autoclave made by Hastelloy, to react them at a stirring rate of 600 rpm and at 30° C. with supplying hydrogen under a constant pressure of 300 kPa from a hydrogen pressurized vessel. A pressure decrease in the hydrogen pressurized vessel was stopped after the reaction period of 2.5 hours. After the stirring was stopped, the temperature of the autoclave was As shown in Table 1, such results that aniline contents in crystal are low and DAR yields are high were obtained by using acetonitrile, propionitrile and butyronitrile as the solvent for the reduction reaction. In the cases of methanol and ethanol, yields of 4,6-diaminoresorcinol obtained as crystals were low due to much 4,6-diaminoresorcinol dissolved in the filtrate.

EXAMPLE 12

161 g (0.4 mol) of 4,6-bisphenylazoresorcinol (purity: 79.1%), 636 g of acetonitrile, 5.09 g of 5% Pd—C and 38.2 g of active carbon (water content; 50%) were introduced in a 2 l autoclave made by SUS, to react them at a stirring rate of 400 rpm and at 30° C. with supplying hydrogen at a constant pressure of 300 kPa from a hydrogen pressurized vessel. A pressure decrease in the hydrogen pressurized vessel was stopped after the reaction period of 3 hours. After stirring was stopped, the temperature of the autoclave was returned to the room temperature and the reactant was removed after nitrogen substitution. The slurry reactant was separated into a cake and a filtrate by filtration. The cake was washed twice with 77 g and 230 g of acetonitrile. 158.6 g of the wetted product, 704 g of the filtrate and the wash liquid were obtained.

After 4,6-diaminoresorcinol (DAR) and aniline produced in the cake, the filtrate and the wash liquid were converted into their hydrochlorides, they were analyzed by a liquid chromatography to obtain such results that a yield of DAR was 93.8% and a yield of aniline was 3.4% in the cake and a yield of DAR was 1.1% and a yield of aniline was 203.1% in the filtrate. Furthermore, a yield of DAR was 0.1% and a yield of aniline was 6.5% in the wash liquid.

Then, 67.4 g (DAR; 0.16 mol) of the cake was added to a solution of 34.4 g (2.2 times by mole) of 35% hydrochloric acid solution, 153 g of water and 0.61 g of stannous chloride dihydrate, to dissolve at 60° C. for 1 hour. Subsequently, the catalyst and active carbon were separated by filtration. The catalyst and active carbon were washed twice with 15.3 g and 30.7 g of 1% hydrochloric acid solutions.

13.4 g of active carbon (water content; 50%) was added to the thus obtained filtrate and stirred at 80° C. for 2 hours.

Subsequently, after active carbon was separated by hot filtration, 112 g of a 35% hydrochloric acid solution was added to the filtrate, warmed at 80° C. for 20 minutes, and thereafter cooled to 10° C. Deposited crystals were filtered off, washed with 9.2 g of a 20% hydrochloric acid solution and thereafter dried under a reduced pressure at 50° C. for 3 hours, to obtain 24.3 g of 4,6-diaminoresorcinol dihydrochloride (purity; 99.3%).

EXAMPLES 13 AND 14

Reaction and post-treatment operation were carried out similar to Example 1 except that the catalyst was replaced by 1.0 g of 1% Pt—C and 2% Pt/0.5% Re—C, to obtain 9.83 g and 9.61 g of crystals (wetted products), respectively.

Analytical results of these crystals and filtrates are shown in Table 2.

one organic solvent selected from aliphatic nitrile compounds, aliphatic alcohols having 3–5 carbon atoms, ethylene glycol monomethyl ether, ethylene glycol monoethyl ether, diethylene glycol monoethyl ether and dioxane as a reaction solvent in the presence of a filter aid, 4,6-diaminoresorcinol is produced in a high yield and most of 4,6-diaminoresorcinol is separated as a slurry which can be easily filtrated and separated, thus it can be collected by filtration still in the high yield, and furthermore a by-product, an aniline derivative, can be separated in a high recovery rate as a filtrate. Thus, solids (crude crystals) of 4,6-diaminoresorcinol isolated immediately after the reduction reaction can be made with a low aniline derivative content and can be easily purified subsequently with a low purification loss. That is, 4,6-diaminoresorcinol having high purity can be easily obtained in a high purification yield.

What is claimed is:

1. A process for preparation of 4,6-diaminoresorcinol or salts thereof by reducing 4,6-bis(substituted)phenylazoresorcinol expressed by the formula [1]

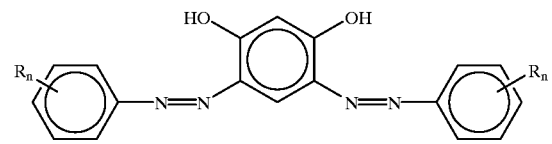

[1]

wherein, R denotes a halogen atom, an alkyl group having 1–5 carbon atoms, a hydroxycarbonyl group or an alkoxy group having 1–5 carbon atoms, n denotes 0 or any integer of 1–5, and two or more groups R may be same or different each other, with hydrogen in the presence of a metal catalyst and a solvent to obtain 4,6-diaminoresorcinol or salts thereof, characterized in that the reduction is carried out in the presence of an aliphatic nitrile compound as the solvent.

2. A process for preparation of 4,6-diaminoresorcinol or salts thereof by reducing 4,6-bis(substituted)phenylazoresorcinol expressed by the formula [1]

TABLE 2

| | | DAR yield % | | | Aniline yield % | | |
|---|---|---|---|---|---|---|---|
| Example | Catalyst | Crystal | Filtrate | Total | Crystal | Filtrate | Total |
| 13 | 1%Pt—C | 93.6 | 4.8 | 98.4 | 1.6 | 222.1 | 223.7 |
| 14 | 2%Pt/0.5%Re—C | 92.9 | 4.7 | 97.6 | 1.3 | 224.1 | 225.4 |

INDUSTRIAL APPLICABILITY

By carrying out the reduction with using an aliphatic nitrile compound as a reaction solvent or with using at least

[1]

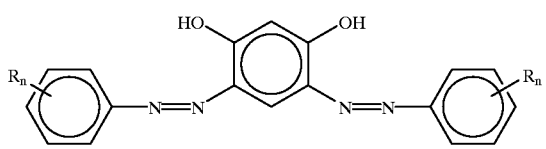

wherein, R denotes a halogen atom, an alkyl group having 1–5 carbon atoms, a hydroxycarbonyl group or an alkoxy group having 1–5 carbon atoms, n denotes 0 or any integer of 1–5, and two or more groups R may be same or different each other, with hydrogen in the presence of a metal catalyst and a solvent to obtain 4,6-diaminoresorcinol or salts thereof, characterized in that the reduction is carried out by using at least one organic solvent selected from aliphatic nitrile compounds, aliphatic alcohols having 3–5 carbon atoms, ethylene glycol monomethyl ether, ethylene glycol monoethyl ether, diethylene glycol monoethyl ether and dioxane as the solvent and furthermore in the presence of a filter aid.

3. A process for preparation of 4,6-diaminoresorcinol or salts thereof according to claim 1, wherein the aliphatic nitrile compounds are monocyanohydrocarbon compounds having 2–6 carbon atoms.

4. A process for preparation of 4,6-diaminoresorcinol or salts thereof according to claim 1, wherein the metal catalyst is at least one metal selected from copper and the Group 8 elements in the periodic table.

5. A process for preparation of 4,6-diaminoresorcinol or salts thereof according to claim 1, wherein the metal catalyst is platinum.

6. A process for preparation of 4,6-diaminoresorcinol or salts thereof according to claim 1, wherein the metal catalyst is a multi-elemental catalyst of platinum, ruthenium or palladium to which at least one element selected from rhenium, indium, tin, antimony, germanium, iridium and rhodium is added.

7. A process for preparation of 4,6-diaminoresorcinol or salts thereof according to claim 2, wherein an amount of the filter aid is 1–100% by weight relative to 4,6-bis(substituted) phenylazoresorcinol.

8. A process for preparation of 4,6-diaminoresorcinol or salts thereof characterized in that the reduced reaction solution obtained by the process according to claim 1 is cooled, deposited solids are filtered under an inert atmosphere, hydrochloric acid is added in a 2 or more times by mole relative to 4,6-bis(substituted)phenylazoresorcinol in the obtained solids to dissolve with heating, and if any insoluble is present, filtration is carried out, furthermore concentrated hydrochloric acid is added and cooled to deposit solids, which are collected by filtration and dried.

9. A process for preparation of 4,6-diaminoresorcinol or salts thereof according to claim 2, wherein the aliphatic nitrile compounds are monocyanohydrocarbon compounds having 2–6 carbon atoms.

10. A process for preparation of 4,6-diaminoresorcinol or salts thereof according to claim 2, wherein the metal catalyst is at least on metal selected from copper and the Group 8 elements in the periodic table.

11. A process for preparation of 4,6-diaminoresorcinol or salts thereof according to claim 2, wherein the metal catalyst is platinum.

12. A process for preparation of 4,6-diaminoresorcinol or salts thereof according to claim 2, wherein the metal catalyst is a multi-element catalyst of platinum, ruthenium or palladium to which at least one element selected from rhenium, indium, tin, antimony, germanium, iridium and rhodium is added.

13. A process for preparation of 4,6-diaminoresorcinol or salts thereof characterized in that the reduced reaction solution obtained by the process according to claim 2 is cooled, deposited solids are filtered under an inert atmosphere, hydrochloric acid is added in a 2 or more times by mole relative to 4,6-bis (substituted) phenylazoresorcinol in the obtained solids to dissolve with heating, and if any insoluble is present, filtration is carried out, furthermore concentrated hydrochloric acid is added and cooled to deposit solids, which are collected by filtration and dried.

14. A process for preparation of 4,6-diaminoresorcinol or salts thereof characterized in that the reduced reaction solution obtained by the process according to claim 3 is cooled, deposited solids are filtered under an inert atmosphere, hydrochloric acid is added in a 2 or more times by mole relative to 4,6-bis (substituted) phenylazoresorcinol in the obtained solids to dissolve with heating, and if any insoluble is present, filtration is carried out, furthermore concentrated hydrochloric acid is added and cooled to deposit solids, which are collected by filtration and dried.

15. A process for preparation of 4,6-diaminoresorcinol or salts thereof characterized in that the reduced reaction solution obtained by the process according to claim 4 is cooled, deposited solids are filtered under an inert atmosphere, hydrochloric acid is added in a 2 or more times by mole relative to 4,6-bis (substituted) phenylazoresorcinol in the obtained solids to dissolve with heating, and if any insoluble is present, filtration is carried out, furthermore concentrated hydrochloric acid is added and cooled to deposit solids, which are collected by filtration and dried.

16. A process for preparation of 4,6-diaminoresorcinol or salts thereof characterized in that the reduced reaction solution obtained by the process according to claim 5 is cooled, deposited solids are filtered under an inert atmosphere, hydrochloric acid is added in a 2 or more times by mole relative to 4, 6-bis (substituted) phenylazoresorcinol in the obtained solids to dissolve with heating, and if any insoluble is present, filtration is carried out, furthermore concentrated hydrochloric acid is added and cooled to deposit solids, which are collected by filtration and dried.

17. A process for preparation of 4,6-diaminoresorcinol or salts thereof characterized in that the reduced reaction solution obtained by the process according to claim 6 is cooled, deposited solids are filtered under an inert atmosphere, hydrochloric acid is added in a 2 or more times by mole relative to 4,6-bis (substituted) phenylazoresorcinol in the obtained solids to dissolve with heating, and if any insoluble is present, filtration is carried out, furthermore concentrated hydrochloric acid is added and cooled to deposit solids, which are collected by filtration and dried.

* * * * *

UNITED STATES PATENT AND TRADEMARK OFFICE
CERTIFICATE OF CORRECTION

PATENT NO. : 6,222,074 B1
DATED : April 24, 2001
INVENTOR(S) : Kenichi Tokunaga et al.

It is certified that error appears in the above-identified patent and that said Letters Patent is hereby corrected as shown below:

<u>Column 11,</u>
Line 6, please replace "4,6-bis(substituted)phenylazoresorinol" with
-- 4,6-diaminoresorcinol --.

Signed and Sealed this

Twenty-sixth Day of July, 2005

JON W. DUDAS
*Director of the United States Patent and Trademark Office*